US012708644B2

(12) United States Patent
Spisek et al.

(10) Patent No.: US 12,708,644 B2
(45) Date of Patent: Aug. 18, 2026

(54) DENDRITIC CELL VACCINATION SEQUENTIAL TO CHEMOTHERAPY

(71) Applicant: Excoso a.s., Prague (CZ)

(72) Inventors: Radek Spisek, Prague (CZ); Jirina Bartunkova, Prague (CZ)

(73) Assignee: Excoso a.s., Prague (CZ)

( * ) Notice: Subject to any disclaimer, the term of this patent is extended or adjusted under 35 U.S.C. 154(b) by 494 days.

(21) Appl. No.: 16/964,847

(22) PCT Filed: Jan. 25, 2019

(86) PCT No.: PCT/EP2019/051840
§ 371 (c)(1),
(2) Date: Jul. 24, 2020

(87) PCT Pub. No.: WO2019/145469
PCT Pub. Date: Aug. 1, 2019

(65) Prior Publication Data

US 2021/0060145 A1 Mar. 4, 2021

(30) Foreign Application Priority Data

Jan. 25, 2018 (EP) .................................... 18153412

(51) Int. Cl.

| | |
|---|---|
| ***A61K 40/19*** | (2025.01) |
| ***A61K 31/337*** | (2006.01) |
| ***A61K 31/555*** | (2006.01) |
| ***A61K 31/7068*** | (2006.01) |
| ***A61K 33/243*** | (2019.01) |
| ***A61K 39/00*** | (2006.01) |
| ***A61K 40/24*** | (2025.01) |
| ***A61K 40/42*** | (2025.01) |
| ***A61P 35/00*** | (2006.01) |

(52) U.S. Cl.
CPC .......... *A61K 33/243* (2019.01); *A61K 31/337* (2013.01); *A61K 31/555* (2013.01); *A61K 31/7068* (2013.01); *A61K 40/19* (2025.01); *A61K 40/24* (2025.01); *A61K 40/42* (2025.01); *A61P 35/00* (2018.01); *A61K 2039/545* (2013.01); *A61K 2039/892* (2018.08); *A61K 2239/31* (2023.05); *A61K 2239/59* (2023.05)

(58) Field of Classification Search
CPC ........ A61K 39/0011; A61K 2039/5152; A61K 2039/892; A61K 2039/5154; A61K 33/243; A61K 31/337; A61P 35/00
See application file for complete search history.

(56) References Cited

U.S. PATENT DOCUMENTS 6,333,028 B1 * 12/2001 Berd .................. A61K 39/0011
424/193.1

FOREIGN PATENT DOCUMENTS

WO WO-2013004708 A1 * 1/2013 ............ A61K 35/12

OTHER PUBLICATIONS

Tanaka F et al., Int. J. Cancer 101(3), 265-269, Sep. 20, 2002 (Year: 2002).*
Rob et al., J Clin Oncol, 2014, 32(15_suppl), abstract.*
Fukuda et al., Melanoma Res., 2017, March, pp. 1-9.*
Mitchell, A phase 2, single-arm study of an autologous dendritic cell treatment against mucin 1 in patients with advanced epithelial ovarian cancer, J Immuno Therapy Cancer, 2:16, pp. 1-9. (Year: 2014).*
NCT00683241, A Phase I Clinical Trial of Autologous Dendritic Cell Vaccine for Recurrent Ovarian or Primary Peritoneal Cancer, pub. date: Feb. 26, 2013. (Year: 2013).*
NCT00799110 (version 15), Vaccination of Patients With Ovarian Cancer With Dendritic Cell/Tumor Fusions With Granulocyte MacrophageColony-stimulating Factor (GM-CSF) and Imiquimod, pub. date Jan. 21, 2016 (Year: 2016).*
Wu et al., The immunologic aspects in advanced ovarian cancer patients treated with paclitaxel and carboplatin chemotherapy, Cancer Immunol Immunother, 2010, 59:279-291. (Year: 2010).*
Public Disclosure Summary SOV03, Version 1.0, Jul. 26, 2017, pp. 1-9.*
Nct02107937, version 8, Phase II Study DCVAC/OvCa Added to First Line Carboplatin and Paclitaxel Newly DiagnosedEpithelial Ovarian Carcinoma, Nov. 29, 2016.*
"Table S1: Patient Characteristics", supplementary information belonging to the Van Tendeloo article vol. 107, No. 31, pp. 13824-13829, 2010, retrieved from https://www.pnas.org/content/suppl/2010/07/13/1008051107.DCSupplemental, (1 page).
Bakhshi et al., "Sex-specific outcomes in cancer therapy: the central role of hormones," Frontiers in Medical Technology, Feb. 1, 2024, (12 pages).
Pepa et al., "Ovarian cancer standard of care: are there real alternatives?," Chinese Journal of Cancer, vol. 34, Issue 1, pp. 17-27, 2015, (11 pages).
Tan et al., "Androgen receptor: structure, role in prostate cancer and drug discovery," Acta Pharmacologica Sinica vol. 36, pp. 3-23, 2015, (21 pages).
Melao, A. "SOTIO Enrolls First Patient in Another Phase 2 Trial of its Ovarian Cancer Immunotherapy", Nov. 29, 2017, retrieved from ovariancancernewstoday.com/2017/11/29/sotio-starts-another-phase-2-trial-of-its-ovarian-cancer-immunotherapy/, (2 pages).
International Search Report for International Application No. PCT/EP2019/051840, mailed Apr. 2, 2019 (4 pages).
Extended European Search Report for European Application No. 18153412.4, mailed Jul. 3, 2018 (10 pages).
Alfaro et al., "Pilot Clinical Trial of Type 1. Dendritic Cells Loaded with Autologous Tumor Lysates Combined with GM-CSF, Pegylated IFN, and Cyclophosphamide for Metastatic Cancer Patients", The Journal of Immunology, vol. 187, No. 11, pp. 6130-6142, 2011, (14 pages).

(Continued)

*Primary Examiner* — Hong Sang
(74) *Attorney, Agent, or Firm* — Kagan Binder, PLLC

(57) ABSTRACT

The present invention relates to the use of a dendritic cell vaccination sequential to chemotherapy, wherein the dendritic cell vaccine is administered to a patient after completion of chemotherapy with at least one chemotherapeutic agent.

8 Claims, 3 Drawing Sheets

(56) References Cited

OTHER PUBLICATIONS

Bloy et al., "Trial watch: Dendritic cell-based anticancer therapy", Oncoimmunology, vol. 3, No. 11, pp. 1-16, 2014, (16 pages).
Chu et al., "Phase I/II randomized trial of dendritic cell vaccination with or without cyclophosphamide for consolidation therapy of advanced ovarian cancer in first or second remission", Cancer Immunol Immunother, vol. 61, No. 5, pp. 629-641, 2011, (14 pages).
Dong et al., "Combination of DC Vaccine and Conventional Chemotherapeutics", Anti-Cancer Agents in Medicinal Chemistry, vol. 16, No. 5, pp. 558-567, 2016, (10 pages).
Koido et al., "Treatment with chemotherapy and Dendritic Cells Pulsed with Multiple Wilms' Tumor 1 (WT1)-Specific MHC Class I/II- Restricted Epitopes for Pancreatic Cancer", Clinical Cancer Research, vol. 20, No. 16, pp. 4228-4239, 2014, (14 pages).
Krishnadas et al., "Complete Remission Following Decitabine/ Dendritic Cell Vaccine for Relapsed Neuroblastoma", Pediatrics, vol. 131, No. 1, pp. 336-341, 2012, (10 pages).
Morse et al., "A Randomized Phase II Study of Immunization with Dendritic Cells Modified with Poxvectors Encoding CEA and MUC1 compared with the same Poxvectors Plus GM-CSF for Resected Metastatic Colorectal Cancer", Annals of Surgery, vol. 258, No. 6, pp. 879-886, 2013, (8 pages).
Fucikova et al., "Phase I/II trial of dendritic cell-based active cellular immunotherapy with DCVAC/PCa in patients with ising PSA after primary prostatectomy or salvage radiotherapy for the treatment of prostate cancer", Cancer Immunol Immunother. vol. 67, No. 1, pp. 89-100, 2017, (12 pages).
Rozkova et al., "FOCUS on FOCIS: Combined chemo-immunotherapy for the treatment of hormone-refractory metastatic prostate cancer", Clinical Immunology, vol. 131, No. 1, pp. 1-10, 2009, (10 pages).
Tanaka et al., "Intratumoral injection of dendritic cells after treatment of anticancer drugs induces tumor-specific antitumor effect in vivo", International Journal of Cancer, vol. 101, No. 3, 2002, (6 pages).
Van Tendeloo et al., "Induction of complete and molecular remissions in acute myloid leukemia by Wilms' tumor 1 antigen-targeted dendritic cell vaccination", vol. 107, No. 31, pp. 13824-13829, 2010, (6 pages).

* cited by examiner

DENDRITIC CELL VACCINATION SEQUENTIAL TO CHEMOTHERAPY

CROSS-REFERENCE TO RELATED APPLICATIONS

This application claims priority to International Application No. PCT/EP2019/051840, filed Jan. 25, 2019 and titled "DENDRITIC CELL VACCINATION SEQUENTIAL TO CHEMOTHERAPY," which in turn claims priority from a European Patent Application having Ser. No. 18153412.4, filed Jan. 25, 2018, titled "DENDRITIC CELL VACCINATION SEQUENTIAL TO CHEMOTHERAPY," both of which are incorporated herein by reference in their entireties.

The immune system is a powerful tool that, if better harnessed, could enhance the efficacy of cytotoxic agents and improve outcomes for cancer sufferers. Vaccination is hoped to be an effective method of harnessing the immune system to eliminate cancer cells. Its activity is mostly dependent on antigen-specific $CD8^+$ T cells that generate cytotoxic T lymphocytes (CTLs) to reject cancer (Palucka and Banchereau 2013). The immune system's components necessary for the induction of such $CD8^+$ T cells include the presentation of antigens by appropriate antigen-presenting cells (APCs). Dendritic cells (DCs) are the most efficient APCs, and are an essential component of vaccination through their capacity to capture, process, and present antigens to T cells (Banchereau and Steinman 1998). Multiple cancer vaccination strategies based on DCs have been developed (Galluzzi et al. 2012). One strategy is to culture patient-derived (autologous) monocytes with specific cytokine combinations, load them with tumor-associated antigen (TAAs) ex vivo in the presence of adjuvants to promote DC maturation and eventually re-administer them into the patient. Other strategies are to deliver TAAs to DCs in vivo or approaches based on DC-derived exosomes (Galluzzi et al. 2012). These strategies have been tested in multiple clinical trials, ranging over a large variety of cancers (Galluzzi et al. 2012; Vacchelli et al. 2013; Bloy et al. 2014; Garg et al. 2017). However, these DC vaccines tested in clinical trials have demonstrated relatively poor therapeutic efficacy. Poor efficacy may be related to many reasons, such as maturation agents used during the DC vaccine preparation, limited immunogenicity of the TAAs loaded upon the DCs, sub-optimal localization in vivo of the administered DCs, and/or formulation of the DC vaccines (Galluzzi et al. 2012). Poor efficacy may also be related to clinical trial designs, where the treatment usually includes concomitant standard of care chemotherapy. It has been shown that after chemotherapy, immune system recovery may be slower than initially believed (Verma et al. 2016), possibly further compromising the efficiency of a DC vaccine when combined with chemotherapy. This may highlight the importance of the timing and scheduling of a DC vaccine administration when the cancer treatment includes standard of care chemotherapy.

On the other hand, despite great efforts to optimize first-line cancer treatment and to devise an optimal therapeutic approach to overcome the risk of a possible relapse after chemotherapy, there are still many cancer indications with a high medical need and only a limited number of treatment options remain available to patients with relapsed disease. The majority of such patients will eventually die. DC vaccines may be a novel therapeutic option for such cancer patients, which could improve their life expectancy and quality of life due to an expected very moderate side effect profile compared to e.g. standard chemotherapeutic agents. But the hope pinned on DC vaccines so far has not delivered significant improvements to the patients with only one approved DC vaccine, sipuleucel T, which was able to show some additional benefit, which however was rated not quantifiable by the German Institute for Quality and Efficiency in Health Care (IQWIQ) (Press release "Sipuleucel-T in prostate cancer: indication of added benefit" of the IQWIQ dated 19 Mar. 2015; www.iqwig.de/en/press/press-releases/press-releases/sipulueel-t-in-prostate-eaneer-in-dieation-of-added-benefit; retrieved 12 Dec. 2017).

Besides the identification of optimized manufacturing protocols for DC vaccines, the investigation of optimal treatment schedules in combination with standard chemotherapies may be a solution to establish DC vaccines as an effective further treatment option in order to prolong the disease-free interval to the next recurrence and next-line treatment and to improve survival of patients.

The inventors have now surprisingly identified that a DC vaccine administered sequentially with chemotherapy, i.e. after completion of chemotherapy, was more beneficial for the overall survival of cancer patients than a DC vaccine administered in parallel to chemotherapy, when compared to standard of care chemotherapy.

Definitions

"Dendritic cell vaccine" or "DC vaccine" refers to human DCs for therapeutic use that may be administered, being prepared without an antigen source or with an antigen source. Preferably, the DCs have been prepared by loading the DCs with an antigen sourced from tumor associated peptide(s), whole antigens from DNA or RNA, whole antigen-protein, idiotype protein, tumor lysate, whole tumor cells or viral vector-delivered whole antigen and subsequently optionally matured with toll-like receptor agonists. More preferably, the DCs have been loaded with whole tumor cells undergoing immunogenic cell death as described for example in (Fucikova et al. 2014). Further, the loaded DCs may be further matured. Maturation occurs e.g. by culturing the loaded DCs in the presence of maturation factors such as Toll-like receptor (TLR) agonists (e.g., poly[I:C] or LPS as further specified below).

The term "Toll-like receptor agonists" refers to molecules binding toll-like receptors (TLR), e.g. lipopolysaccharides (LPS) binding to TLR4, double-stranded RNA or polyinosinic:polycytidylic acid (poly[I:C]) binding to TLR3.

"Chemotherapy" is a treatment that uses drugs or agents to stop the growth of cancer cells, either by killing the cells (cytotoxic agents) or by stopping them from dividing (cytostatic agents). Chemotherapeutic agents may include alkylating agents or alkylating-like agents such as carboplatin or cisplatin, antimetabolites such as gemcitabine, pemetrexed, methotrexate, anti-tumor antibiotics such as doxorubicin, topoisomerase inhibitors such as topotecan, irinotecan or etoposide, mitotic inhibitors such as docetaxel, paclitaxel, vinblastine, or vinorelbine, Further examples of chemotherapeutic agents are provided by the American Cancer Society and can be found here: www.cancer.org/treatment/treatments-and-side-effects/treatment-types/chemotherapy/how-chemotherapy-drugs-work.html ('American Cancer Society—How Chemotherapy Drugs Work' 2016). Such drugs may typically be small molecule drugs (organic compounds of low molecular weight, e.g. <900 Dalton). For the purposes of the present invention the term "chemotherapy" is not meant to include agents used in maintenance therapies as defined herein. Chemotherapy may be given orally, by injection, or infusion, or on the skin, depending on the type and stage of the cancer being treated. It may be given alone or in combination with other types of treatments, such as surgery, radiation therapy, biologic therapy or small molecule drugs that specifically target the cancer cells than chemotherapeutic agents, e.g. by interacting with target molecules that are more highly expressed in cancer cells than in other types of cells.

In the context of the present invention, the term "chemotherapy" in a preferred embodiment excludes any agents which are used in the context of cancer therapy to reduce a regulatory T cell response. Thus, in one embodiment of the present invention, the chemotherapeutic agent is not cyclophosphamide (Berd and Mastrangelo 1987; Fucikova et al. 2017).

"Adjuvant chemotherapy" is a chemotherapy treatment given after a primary treatment (for example surgery or radiation, i.e. a cancer treatment other than chemotherapy) to treat residual tumor and/or to prevent or treat metastasis. In the context of the present invention, dendritic cell vaccines are considered not to be adjuvant chemotherapy.

Chemotherapy is typically given in cycles: a treatment period is followed by a recovery period, then another treatment period, and so on. A "cycle" is thus one treatment period followed by one recovery period.

Multiple drugs can be given as "combination chemotherapy" to treat the same disease.

"Completion" of chemotherapy is achieved when the last administration of the chemotherapy within the last cycle is completed. For the avoidance of doubt, the last cycle may be the last scheduled cycle or, if chemotherapy is "terminated" (e.g. prior to completion due to undesired side effects or non-response to the treatment), it is the last administered cycle.

"Maintenance therapy" or "maintenance treatment" is a treatment following the initial chemotherapy or starting within the initial chemotherapy after complete remission or partial response (Sakarya 2016; Ellis 2016). It is given to help keeping cancer from coming back after it has disappeared or shrunk. Maintenance treatment does not involve the use of a chemotherapeutic agent, e.g. as in adjuvant chemotherapy. It may include treatment with selected drugs with moderate side effects, such as hormones and hormone analogous (e.g. enzalutamide, abiraterone, tamoxifen, LHRH agonists and antagonists), kinase inhibitors (e.g. erlotinib, afatinib, gefitinib, crizotinib, alectinib, ceritinib, dabrafenib, trametinib and osimertinib), PARP inhibitors (e.g. olaparib, niraparib), vaccines including DC vaccines, or biologics (e.g. antibodies as for example bevacizumab, pembrolizumab, nivolumab). Thus, the maintenance treatment has the goal of maintaining the complete remission or partial remission state of the patient. Preferably, it may be given for extended periods of time without causing adverse events leading to termination of the treatment typically until progression of the disease. Excluded from maintenance therapy are interferon/hydroxycloroquine (IFN/HCQ) treatments. Preferably, the initial chemotherapy is adjuvant chemotherapy.

A DC vaccine can in principle be administered to a patient after completion of chemotherapy, i.e. "sequentially", or the administration may be started while the chemotherapy is ongoing and is then given in "parallel". For the purposes of the present invention, the DC vaccine treatment is given sequentially, i. e. subsequent to chemotherapy when chemotherapy has been completed.

A patient will "respond" to chemotherapy if the treatment is effective, i.e. the tumor does not further grow and/or metastasize or the tumor is decreasing in size.

A patient will be "refractory" to chemotherapy if he or she does not respond to the treatment from the beginning or during the course of the chemotherapy, meaning that the cancer is or becomes resistant to the chemotherapeutic drug.

A treated cancer may "relapse" or be "recurrent" when the cancer or signs and symptoms of the cancer return after a period of improvement.

A "biologic" is a substance that is often recombinantly expressed and is used in the prevention, diagnosis or treatment of cancer and other diseases. Biologic agents include antibodies, nucleic acid-based drugs, fusion proteins, hormones or hormone analogs or cytokines. In contrast to most small molecule chemotherapeutic agents that are chemically synthesized and where their structure is known, most biologics are complex mixtures and/or post-translationally modified substances that are not easily identified or characterized. Biological products, including those manufactured by biotechnological methods, tend to be heat sensitive and susceptible to microbial contamination. In a preferred embodiment of the present invention, a biologic agent is not a virus.

"First-line therapy" is the first treatment given for a disease. It is often part of a standard set of treatments, such as surgery followed by chemotherapy and radiation. When used by itself, first-line therapy is typically the one accepted as the best treatment for a disease. If it does not cure the disease or if it causes severe side effects, other treatment options may be added or used instead. The first-line therapy can also be called induction therapy, primary therapy, or primary treatment.

A "first-line chemotherapy" is the therapy with at least one chemotherapeutic agent as part of a first-line therapy. It is understood that "first-line chemotherapy" excludes a parallel use of a dendritic cell vaccine therapy.

"Second-line chemotherapy" is the chemotherapy that is given when the patient does not respond to the initial treatment (first-line therapy), or if the first-line therapy stops being effective. "Third-line chemotherapy" is the chemotherapy that is given when both initial treatment (first-line therapy) and subsequent treatment (second-line therapy) were not effective or stopped being effective.

"Overall survival" (OS) is the length of time from either the date of diagnosis, date of randomization or the start of treatment for a disease, such as cancer, that patients diagnosed with the disease are still alive. In a clinical trial, measuring the overall survival is one way to measure the efficacy of a new treatment.

"Randomization" into a clinical trial is the process by which subjects are assigned by chance to separate groups that compare different treatments or other interventions. Randomization gives each participant an equal chance of being assigned to any of the groups.

"Overall survival rate" is the percentage of people in a study or treatment group who are still alive for a certain period of time after they were diagnosed with a disease, randomized or started treatment for a disease, such as cancer. The overall survival rate is often stated as a five-year survival rate, which is the percentage of people in a study or treatment group who are alive five years after their diagnosis or the start of treatment.

"Progression-free survival" (PFS) is the length of time during and after the treatment of a disease, such as cancer, that a patient lives with the disease but it does not get worse.

In a clinical trial, measuring the progression-free survival is one way to see how well a new treatment works.

A patient is "cured" from cancer when the patient is in complete remission and all signs and symptoms of cancer have disappeared. In a preferred embodiment, a patient is considered as "cured" if he/she remains in complete remission for 5 years or more. Thus, a therapy "failed to cure" a patient, if for example the patient is not in complete remission, if the patient relapsed or if the cancer is refractory.

"Standard of care" is a treatment that is accepted by medical experts as a proper treatment for a certain type of disease and that is widely used by healthcare professionals. It can also be called best practice, standard medical care, or standard therapy.

A "serious adverse event" (SEA) is any serious undesirable experience associated with the use of a medical product in a patient. The event is serious when the patient outcome is life-threatening, death, hospitalization/prolongation of hospitalization, congenial anomaly, persistent or significant disability/incapacity requiring intervention to prevent permanent impairment/damage or is an important medical event (e.g. serious problems with breathing, blood disorders, seizures/convulsions, drug dependence).

The term "immediately", as in "immediately after the completion of the last cycle of chemotherapy", refers to a time period of about 1 week, preferably 3 days and more preferably one day.

The term "dose" means a measured, defined amount of a drug or DC vaccine administered in a given time, e.g. a daily dose of x cells.

The term "tumor associated peptide(s)" means a peptide that may be associated with a tumor. The presence of the peptide may be highly correlated with the presence of certain tumor cells. They may be highly specific for a certain tumor but the tumor associated peptides may also be related to different tumors. Further, the peptides may also be present not only in tumor cells but also in normal cells, but the tumor associated peptide are then expressed in higher amounts in tumor cells. The tumor associated peptides may also comprise only a partial sequences of a larger tumor associated protein, i.e. a "whole" tumor associated protein. Tumor associated peptides may be isolated from respective tumor cells or they may be produced as recombinant peptides.

The term "whole antigens from DNA or RNA" refers to the case wherein the dendritic cell is loaded with DNA or RNA that encodes the sequence of a whole antigen.

The term "whole antigen-protein" means that the antigen comprises the full-length sequence of a protein of interest as the antigen and not only peptide-epitopes derived from the full-length protein.

The term "idiotype protein" refers to the idiotype target protein, which is composed of the unique antigenic determinants in the variable regions of e.g. clonal immunoglobulin (Ig) expressed by the tumor cells.

The term "tumor lysate" refers to a composition comprising tumor cells and a lysate buffer, wherein the lysate buffer contains agents that lyse the tumor cells. Intracellular, transmembrane and/or extracellular components of the tumor may thus be present in the tumor lysate and serve as antigens in accordance with the present invention.

The term "whole tumor cells" refers to the use of complete tumor cells that have not been lysed in a lysate buffer.

The term "viral vector-delivered whole antigen" means that the antigen is delivered to the dendritic cell by using a viral vector. For example, the whole antigen may be a whole protein and the viral vector encodes the protein and the protein is thus expressed in the dendritic cell after transfection with the viral vector.

The term "taxane" refers to a compound class of diterpenes that feature a taxadiene core structure. Examples of taxanes include, but are not limited to, paclitaxel, docetaxel and cabazitaxel.

The term "platinum complex" refers to metal complex compound, wherein the platinum is the metal component. The platinum may for example be complexed by oxygen or nitrogen atoms of one or more organic or inorganic compounds to form the platinum complex. Examples of platinum complexes include, but are not limited to, carboplatin and cisplatin.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless something else is specifically stated.

Technical terms are used by their common sense. If a specific meaning is conveyed to certain terms, definitions of terms will be given in the following in the context of which the terms are used.

DESCRIPTION OF THE INVENTION

In a first aspect, the invention relates to a dendritic cell vaccine (DC vaccine) for use in the treatment of cancer, wherein the dendritic cell vaccine is administered to a patient after completion of chemotherapy with at least one chemotherapeutic agent. The chemotherapeutic agent or agents to be used may be determined by the qualified practitioner, and may be part of the standard of care recommended for the type of cancer to be treated. Depending on the standard of care, the chemotherapeutic agent/s may be administered in one or multiple cycles. The duration, frequency and number of cycles will depend on the cancer to be treated and on the agent/s used. The chemotherapeutic agent/s may all be given on a single day, several consecutive days, or continuously, to an outpatient or to an inpatient. Treatment could last minutes, hours, or days, depending on the specific protocol. Chemotherapy may be repeated weekly, bi-weekly, or monthly. Usually, a cycle is defined in monthly intervals. For example, two bi-weekly chemotherapy sessions followed by a recovery period may be classified as one cycle. In most cases, the total number of cycles—or the length of chemotherapy from start to finish—has been determined by research and clinical trials. As long as there are detectable signs of cancer, the length of chemotherapy treatment will depend upon the response of the cancer to therapy. If the cancer disappears completely (complete response), chemotherapy may continue for 1-2 cycles beyond this observation to maximize the chance of having attacked all microscopic, i.e. undetectable, tumors. If the cancer shrinks but does not disappear (partial response), chemotherapy may continue as long as it is tolerated and the cancer does not grow (progression).

If the cancer continues to grow, the chemotherapy will be terminated and the patient will be considered as refractory to such chemotherapy and such chemotherapy will be considered as completed. Chemotherapy will also be considered as completed when the last administration of the chemotherapy within the last cycle is completed.

It has surprisingly been found that first line cancer patients, who completed chemotherapy and received the DC vaccine only after completion (sequentially), had a statistically significant longer overall survival compared to both the control group (only chemotherapy) and a group of patients having received the chemotherapy and the DC vaccine in parallel (see FIGS. 2 and 3). Most unusually even after more than 3.5 years after inclusion into the study, none of the patients from the sequential treatment arm has died to date (per-protocol population), whereas about 40% of patients having received standard of care, in this case carboplatin and paclitaxel, and about 30% of patients from the parallel treatment arm have died (see FIG. 3). Accordingly, in the context of the present invention, it appears to be crucial that the DC vaccine will only be applied after the completion of the chemotherapy. The term "completion of chemotherapy" is understood to apply only to patients who responded to the chemotherapy treatment.

The DC vaccine may be formulated for intravenous, intradermal or subcutaneous administrations, preferably for subcutaneous administration. The DC vaccine can be formulated for example for infusion or bolus injection, and may be administered together with an adjuvant (Elster, Krishnadas, and Lucas 2016). Administration can be systemic, loco-regional or local. When one dose is injected, the dose can be administered in one or multiple injections, preferably in two injections. Preferably, the DC vaccine may be administered to the patient subcutaneously into lymph-node regions close to the region where the cancer to be treated is developing. Various delivery systems are known and can be used to deliver the DC vaccine. The mode of administration may be left to the discretion of the practitioner.

In the context of the present invention, the term chemotherapy (drugs killing tumor cells or stopping them from dividing) is understood to include only drugs which are prescribed to the patient in order to act on the tumor cells, e.g. stopping the growth of or killing tumor cells. Therefore, the term chemotherapy is understood to relate to the class of compounds used for cytostatic or cytotoxic agents as chemotherapeutic agents. In a preferred embodiment, the at least one chemotherapeutic agent is selected from carboplatin, cisplatin, paclitaxel, docetaxel, gemcitabine, pegylated liposomal doxorubicin, etoposide, topotecan, irinotecan, trabectedin, mitoxantrone, cabazitaxel, vinorelbine, pemetrexed, vinblastine and albumin-bound paclitaxel. The specific regimen of chemotherapy may be dictated by the established standard of care of the specific cancer to be treated, and may be at the discretion of the practitioner. In a preferred embodiment, the chemotherapeutic agent is not cyclophosphamide. In a particularly preferred embodiment, the chemotherapeutic agent is not a low dose regimen of cyclophosphamide, when it is used to reduce the function of regulatory T cells as described in Berd et al and Fucikova et al (Berd and Mastrangelo 1987; Fucikova et al. 2017) and more preferably it is not used prior to DC vaccination (Dong et al. 2016). For the avoidance of doubt, chemotherapy in the meaning of this invention does not include drugs prescribed to treat co-morbidities, to avoid or treat side-effects or help the patient to recover from side-effects (e.g. erythropoietin), or drugs prescribed as maintenance therapy.

The first dose of the DC vaccine is administered to the patient preferably within two months after completion of the last cycle of the chemotherapy, preferably within one month after completion of the last cycle of the chemotherapy, more preferably within two weeks after completion of the last cycle of the chemotherapy, most preferably immediately after the completion of the last cycle of the chemotherapy. The timing between completion of the last cycle of chemotherapy and administration of the DC vaccine may depend on the chemotherapeutic agent/s, on the cancer to be treated, on the reaction of the patient regarding toxicity of the chemotherapeutic agent/s. In a preferred embodiment, the patient received at least 3 cycles of chemotherapy and preferably at least 6 cycles of chemotherapy.

Alternatively, the first dose of the DC vaccine is administered to the patient within two months after administration of the last dose of the chemotherapy, preferably within one month after administration of the last dose of the chemotherapy, more preferably within two weeks after administration of the last dose of the chemotherapy. The last dose may be given within the last cycle of chemotherapy, i.e. before completion of the last chemotherapy cycle.

In a preferred embodiment, the chemotherapy is a first-line chemotherapy. The type of first line treatment will depend on the cancer to be treated and on the stage of the cancer (e.g. the TNM staging system—tumor/lymph nodes/metastasis ('National Cancer Institute—Diagnosis and Staging' 2015) or FIGO staging for ovarian cancer (TIGO ovarian cancer staging' 2014). For example, in the case of first-line treatment of ovarian cancer, a dendritic cell vaccine may be administered after completion of a taxane and a platinum complex combination chemotherapy, especially a paclitaxel and carboplatin combination chemotherapy, or a docetaxel and carboplatin combination chemotherapy. Carboplatin may be given in combination with gemcitabine. Alternatively the chemotherapy combination may be a pegylated liposomal doxorubicin and carboplatin combination. More generally, first-line chemotherapy treatments for use in cancers such as ovarian cancer, prostate cancer and lung cancer, at different stages, where a dendritic cell vaccine may be administered after completion, are described at www.cancertherapyadvisor.com (CancerTherapy Advisor 2017b, 2017c, 2017a). The invention also relates to a DC vaccine treatment administered to a patient after completion of chemotherapy, where a previous chemotherapy treatment failed to cure the patient from cancer. A previous chemotherapy may have failed to cure the patient because the patient relapsed after completion or termination of the previous chemotherapy or because the patient was refractory to the chemotherapy. For example, if such patient underwent second line chemotherapy and, after completion of such second line chemotherapy, he is eligible for receiving the dendritic cell vaccine.

In another aspect, the DC vaccine for use in the treatment of cancer may be administered in combination with a maintenance therapy. Examples for maintenance therapies for ovarian cancer include treatments with bevacizumab (continuation maintenance after $1^{st}$ line carboplatin/paclitaxel treatment), olaparib (after $2^{nd}$ line platinum sensitive treatment and after $3^{rd}$ line treatment) or niraparib (after $3^{rd}$ line treatment). Examples for maintenance therapies for non-small cell adenoma carcinoma lung cancer include treatments with bevacizumab after $1^{st}$ line treatments. In a preferred embodiment, the maintenance therapy comprises the therapy with bevacizumab, olaparib and/or niraparib.

Different types of DC vaccines are well known in the art and can be divided into different groups according to the method how the DCs are loaded or pulsed with tumor antigens (Turns and Rooney 2010; Elster, Krishnadas, and Lucas 2016), incorporated herein by reference. Accordingly, the DC vaccine for use in the treatment of cancer administered to a patient after completion of chemotherapy is a DC vaccine loaded ex-vivo with an antigen source selected from tumor associated peptide(s), whole antigens from DNA or RNA, whole antigen-protein, idiotype protein, tumor lysate, whole tumor cells or viral vector-delivered whole antigen. The DC vaccine may optionally be matured with toll-like receptor agonists (e.g. poly[I:C] or LPS). Preferentially, the DC vaccine is matured with the TLR3 agonist poly[I:C]. Tumor lysate may be autologous or allogeneic/heterologous. Likewise, whole tumor cells may be autologous or allogeneic/heterologous. Whole tumor cells and tumor lysate may originate from one or multiple tumor cell lines, and may be selected for a specific presence of antigens matching the patient's tumor to be treated. The source of antigens may be selected and DCs may be loaded by techniques known to one of skill in the art (Turns and Rooney 2010; Elster, Krishnadas, and Lucas 2016).

In a preferred embodiment of the invention, the antigen source is whole tumor cells and wherein preferably the tumor cells were killed by high hydrostatic pressure (HHP) as described in WO 2013/004708 and WO 2015/097037, incorporated herein by reference (see examples 1 to 4 of WO 2013/004708 and examples 2 and 3 of WO 2015/097037). In brief, whole tumor cells from cell lines or from the patient are treated by HHP between 200 and 300 MPa for 10 min to 2 hour. Such a treatment will induce a specific type of apoptosis called immunogenic cell death in the treated tumor cells which may be characterized by expression of immunogenic molecules on the cell surface such as HSP70, HSP90 and calreticulin and the release of late apoptotic markers HMGB1 and ATP and thus increase the uptake of these cells by DCs, resulting in loaded DCs presenting multiple tumor antigens. Prior to being loaded on DCs, the apoptotic tumor cells may be cryopreserved.

In a preferred embodiment, the whole tumor cells loaded upon the DC vaccine are allogeneic to the patient. Whereas autologous tumor cells purportedly have a better match with the patient's tumor antigens, in practice it is highly complicated to manufacture a DC vaccine from autologous tumor biopsies. Therefore, it is preferred to use allogeneic tumor cells, e.g. tumor cell lines, which have an overlap of expressed tumor antigens with the typical tumor antigens of the tumor disease to be treated.

In turn, the DCs may be derived from monocytes that are autologous to the patient being treated. As used herein, the term "monocytes" refers to leukocytes circulating in the blood characterized by a bean-shaped nucleus and by the absence of granules. Monocytes can give rise to dendritic cells. The monocytes can be isolated from a patient's blood by any technique known to one of skill in the art, the preferred method being leukapheresis. Leukapheresis allows to collect monocytes that are autologous to the patient being treated, to be used for the preparation of the DC vaccine. Leukapheresis may be performed by any technique known to one of skill in the art.

Typically, dendritic cells are derived from monocytes obtained by leukapheresis prior to the chemotherapy, which is followed by the DC vaccination. As many chemotherapies induce neutropenia, a leukapheresis after initiation of chemotherapy may lead to less viable cells and therefore to a lower quantity and/or quality of the DC vaccine.

In another aspect of the invention, 5 to 30 doses of dendritic cell vaccines are administered to the patient and preferentially 8 to 15 doses of dendritic cell vaccines are administered to the patient. In another preferred embodiment, at least 8 doses of dendritic cell vaccines are administered to the patient. During manufacturing, DC vaccines may be aliquoted as multiple doses, each dose containing the same amount of DC. DC vaccine doses can be cryopreserved until use. The number of doses to be administered may be left at the discretion of the treating practitioner. DC vaccine doses may be administered to a patient after completion of chemotherapy preferably at 1 to 6-week intervals between each dose. In a preferred embodiment the DC vaccine doses may be administered at 1-week intervals between each dose, at 2-week intervals, at 3-week intervals, at 5-week intervals or at 6-week intervals, preferably at 3-week intervals. The length of the interval and the number of doses may be determined depending on the cancer to be treated, of the stage of the cancer, on the type of chemotherapy which is part of the treatment or may be left at the discretion of the practitioner. The length of the interval may also change during the treatment, starting with a short interval for the first doses (e.g. 3-week intervals), followed by a longer interval for the late doses (e.g. 6-week intervals). In a preferred embodiment, the dosing regimen is preferably 5 initial doses administered at 3-week intervals and at 6-week intervals thereafter. This dosing regimen is particularly preferred for the treatment of ovarian cancer.

In another embodiment, the invention relates to a DC vaccine treatment of cancer, to be administered to patients after completion of chemotherapy, where the cancer is selected from the group consisting of ovarian cancer, prostate cancer, lung cancer, brain cancer and melanoma. In one embodiment, the cancer to be treated is not a liquid tumor cancer, such as leukemias and lymphomas. It is thus preferred that the cancer is a solid tumor cancer. Ovarian cancer includes epithelial ovarian, fallopian tube, or primary peritoneal cancer and may be stage I to IV according to the International Federation of Gynecology and Obstetrics [FIGO]. Prostate cancer includes acinar adenocarcinoma, ductal adenocarcinoma, transitional cell cancer, squamous cell cancer and small cell cancer and may be graded using the Gleason scoring system. Lung cancer is preferentially non-small cell lung cancer and includes lung adenocarcinoma, squamous cell lung carcinoma and large-cell lung carcinoma. In a preferred embodiment, the cancer to be treated is selected from the group consisting of ovarian cancer, prostate cancer, brain cancer and melanoma.

In another preferred embodiment, the cancer to be treated is ovarian cancer or lung cancer, more preferably newly diagnosed epithelial ovarian carcinoma (i.e. patients never diagnosed before with ovarian cancer), relapsed platinum-sensitive epithelial ovarian carcinoma or stage IV non-small cell lung cancer.

In another preferred embodiment, the cancer is not lung cancer. In another embodiment, the cancer is not stage III non-small cell lung cancer.

In yet another preferred embodiment, the cancer is ovarian cancer, and more preferably newly diagnosed ovarian carcinoma.

In another particularly preferred embodiment, the cancer is recurrent advanced ovarian cancer or relapsed platinum-sensitive ovarian carcinoma.

In a preferred embodiment, the chemotherapy treatment also includes a combination treatment of at least two chemotherapeutic agents. It is particularly preferred that the combination treatment is selected from the following drug combinations: paclitaxel and carboplatin; paclitaxel and cisplatin; docetaxel and carboplatin; cisplatin and vinorelbine; cisplatine and etoposide; cisplatin and gemcitabine; cisplatin and pemetrexed; cisplatin and irinotecan; gemcitabine and docetaxel; carboplatin and etoposide, carboplatin and gemcitabine, carboplatin and pemetrexed and gemcitabine and docetaxel. Combination treatments may be dictated by the established standard of care of the specific cancer to be treated, institutional guidelines and may be at the discretion of practitioner. In a preferred setting for first-line treatment, preferably for the treatment of ovarian cancer, a DC vaccine may be administered after completion of chemotherapy, where the chemotherapy is a taxane and a platinum complex combination, especially the paclitaxel and carboplatin combination. In another preferred setting, especially for the treatment of recurrent advanced ovarian cancer, a DC vaccine may be administered after completion of chemotherapy, where the chemotherapy comprises a platinum complex and gemcitabine combination.

In another preferred embodiment, the chemotherapy treatment for newly diagnosed epithelial ovarian carcinoma is a platinum compound combined with a taxane.

In another particularly preferred embodiment, the chemotherapy treatment for newly diagnosed epithelial ovarian carcinoma is carboplatin combined with paclitaxel.

In yet another embodiment, leukapheresis is performed on patients with newly-diagnosed ovarian cancer prior to the administration of the first cycle of chemotherapy. Following leukapheresis, the collected autologous monocytes are cultivated in the presence of cytokines to obtain immature DCs. Preferred cytokines are GM-SCF and IL-4. The DC vaccine is obtained by loading the immature DCs with tumor cells undergoing ICD, preferably from HHP treated allogeneic tumor cell lines of the same tumor origin as the one to be treated, and further maturation with TLR agonists, preferably poly[I:C] resulting in the DC vaccine, which may be fractioned and stored in individual doses of approximately $1\times10^7$ DCs per dose.

In one embodiment, treatment of the patients starts with first-line chemotherapy (e.g., carboplatin and paclitaxel treatment, e.g., according to the instructions of the marketing authorization). In a preferred embodiment, the treatment of the patients starts with six three-week cycles of first-line chemotherapy. The first DC vaccine administration may occur at the completion of the last chemotherapy cycle. In a preferred embodiment, the first DC vaccine administration occurs two weeks or earlier after administration of the last dose of first-line chemotherapy. About ten doses of DC vaccine may be given at three-week intervals for the first 5 doses and at six-week intervals thereafter. Maintenance treatment, such as bevacizumab, may also be administered in combination with the first line chemotherapy and/or in combination with the DC vaccine.

The invention is also described by the following items:

1. A dendritic cell vaccine for use in the treatment of cancer, wherein the dendritic cell vaccine is administered to a patient after completion of chemotherapy with at least one chemotherapeutic agent.
2. The dendritic cell vaccine for use of item 1, wherein the first dose of the dendritic cell vaccine is administered within two months after completion of the last cycle of the chemotherapy preferably within one month after completion of the last cycle of the chemotherapy, more preferably within two weeks after the completion of the last cycle of the chemotherapy, most preferably immediately after the completion of the last cycle of the chemotherapy.
3. The dendritic cell vaccine for use of item 1, wherein the first dose of the dendritic cell vaccine is administered within two months after administration of the last dose of the chemotherapy, preferably within one month after administration of the last dose of the chemotherapy, more preferably within two weeks after administration of the last dose of the chemotherapy.
4. The dendritic cell vaccine for use of items 1 to 3, where the chemotherapy is a first-line chemotherapy.
5. The dendritic cell vaccine for use of any one of items 1 to 4, wherein a previous chemotherapy treatment failed to cure the patient from cancer.
6. The dendritic cell vaccine for use of any one of items 1 to 5, wherein the dendritic cell vaccine is administered in combination with a maintenance therapy.
7. The dendritic cell vaccine for use according to any one of items 1 to 6, wherein the dendritic cells are loaded ex vivo with an antigen source selected from tumor associated peptide(s), whole antigens from DNA or RNA, whole antigen-protein, idiotype protein, tumor lysate, whole tumor cells or viral vector-delivered whole antigen.
8. The dendritic cell vaccine for use according to item 7, wherein the antigen source is whole tumor cells, and wherein preferably the tumor cells were killed by high hydrostatic pressure.
9. The dendritic cell vaccine for use of any one of items 7 to 8, wherein the whole tumor cells are allogeneic to the patient.
10. The dendritic cell vaccine for use of any one of items 1 to 9, wherein the dendritic cells are derived from monocytes obtained by leukapheresis prior to chemotherapy.
11. The dendritic cell vaccine for use of any one of items 1 to 10, wherein
i) 5 to 30 doses of dendritic cell vaccines are administered and preferentially 8 to 15 doses of dendritic cell vaccines are administered;
ii) the dendritic cell vaccine doses are administered at 1-week intervals, at 2-week intervals, at 3-week intervals, at 5-week intervals or at 6-week intervals; and/or
iii) the dosing schedule comprises 5 initial doses administered at 3-week intervals followed by 5 doses at 3-week intervals or 6-week intervals.
12. The dendritic cell vaccine for use of any one of items 1 to 11, wherein the cancer is selected from the group consisting of ovarian cancer, prostate cancer, lung cancer, brain cancer and melanoma; and wherein preferably the cancer is ovarian cancer; and wherein more preferably the cancer is newly diagnosed ovarian cancer.
13. The dendritic cell vaccine for use of any of the items 1 to 12, where the at least one chemotherapeutic agent is selected from carboplatin, cisplatin, paclitaxel, docetaxel, gemcitabine, pegylated liposomal doxorubicin, etoposide, topotecan, irinotecan, trabectedin, mitoxantrone, cabazitaxel, vinorelbine, pemetrexed, methotrexate, vinblastine, and albumin-bound paclitaxel.
14. The dendritic cell vaccine for use of any one of the items 1 to 13, where the chemotherapy comprises a combination treatment selected from a taxane and a platinum complex; gemcitabine and a platinum complex; cisplatin and vinorelbine; cisplatine and etoposide; cisplatin and pemetrexed; cisplatin and irinotecan; gemcitabine and docetaxel; carboplatin and etoposide; carboplatin and pemetrexed; and gemcitabine and docetaxel, wherein preferably:
i) the chemotherapy comprises chemotherapy with a combination of a taxane and a platinum complex, preferably a taxane and a platinum complex selected from paclitaxel and carboplatin; paclitaxel and cisplatin; and docetaxel and carboplatin; and wherein more preferably the combination is paclitaxel and carboplatin; or ii) the combination is gemcitabine and a platinum complex, wherein preferably the combination is cisplatin and gemcitabine; or carboplatin and gemcitabine.

Schematic diagram of the clinical study on ovarian cancer, comparing the standard of care chemotherapy treatment to the DC vaccine treatment administered in parallel to chemotherapy or sequentially to chemotherapy. "DCVAC OvCa" stands for a DC vaccine where dendritic cells have been loaded with ovarian cancer cells undergoing immunogenic cell death and matured by a Toll-like receptor 3 (TLR-3) ligand, as described in Example 1.

FIG. 2:

Interim analysis of overall survival (OS) in the clinical study for the Intention-to-Treat (ITT) population.

FIG. 3:

Interim analysis of OS in the clinical study for the Per-Protocol (PP) population.

Figure 2:
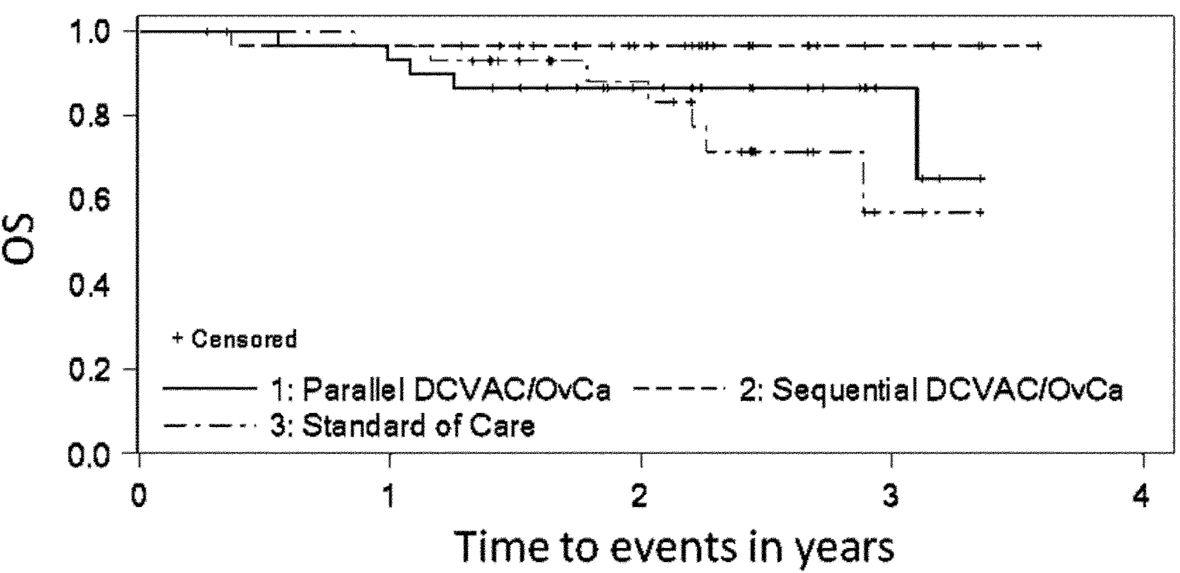
Figure 3:
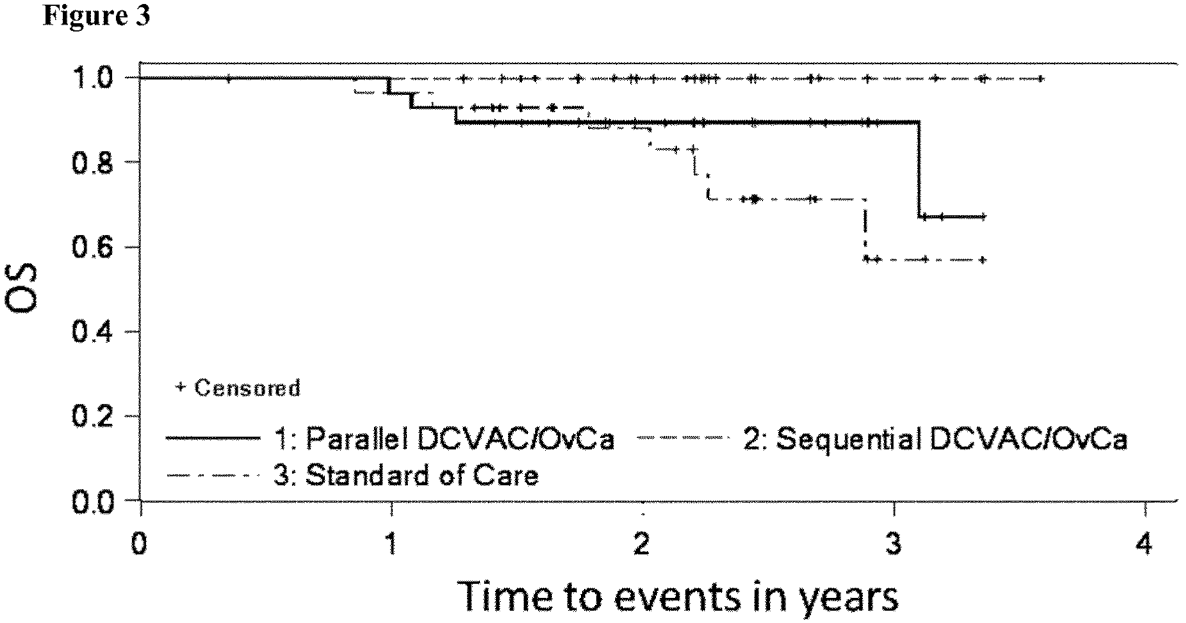

"Censored" in FIGS. 2 and 3 means patients who are still included in the study by the time of reporting. Censored subjects are indicated on the Kaplan-Meier curve as tick marks; these do not terminate the interval.

EXAMPLES

Example 1. DC Vaccine

The DC vaccine consisted of autologous DCs loaded ex vivo with killed ovarian cancer cells and matured by a Toll-like receptor 3 (TLR-3) ligand. DCs were derived from autologous monocytes that were obtained by leukapheresis. Monocytes isolated from the leukapheresis product were cultured in the presence of granulocyte macrophage colony-stimulating factor and interleukin 4 to obtain immature DCs. Immature DCs were loaded with cells of the ovarian cancer cell lines OV-90 and SK-OV-3 (in a ratio of 2:1). Before being added to the DC culture, OV-90 and SK-OV-3 cells were treated with high hydrostatic pressure (HHP) (as described in WO 2013/004708, examples 1-4), which induces immunogenic cell death (Fucikova et al. 2014). The tumor cell-loaded DCs were activated by polyinosinic: polycytidylic acid (poly[I:C]), a TLR-3 ligand.

The final product was cryopreserved in aliquots of approximately $1\times10^7$ DCs per vial in 1 mL of CryoStor CS10 freezing medium containing 10% dimethyl sulfoxide.

DC vaccine aliquots were transported to the study sites on dry ice at a temperature below −50° C. Each DC vaccine aliquot (dose) was then thawed and diluted in saline to a final volume of 5 mL. The diluted dose was administered to the patient subcutaneously in two applications: one into the inguinal area and one into the contralateral axillary area (2.5 mL to each of the application sites).

Example 2. Systemic Standard Therapy in Newly Diagnosed Ovarian Cancer Patients The European Society of Medical Oncology (ESMO) established guidelines (Ledermann et al. 2013) of treatment options for patients with newly diagnosed ovarian cancer.

Stage I

- Surgery is the initial method aiming at resection of the tumour and adequate staging of the disease.
- Adjuvant chemotherapy (after completion of surgery):
  - Platinum-based chemotherapy with carboplatin
  - Combination of carboplatin with paclitaxel Stage II-IV

- Surgery should be focused on complete cytoreduction of all macroscopic disease. Benefit of systematic pelvic and para-aortic lymphadenectomy is considered questionable at this stage.
- Chemotherapy in all patients (after or before surgery)
  - Paclitaxel with carboplatin combination has been the standard of care for over 15 years. Carboplatin can be replaced by cisplatin; however, cisplatin is more toxic and its administration is less convenient.
  - In case of paclitaxel toxicity, docetaxel in combination with carboplatin or pegylated liposomal doxorubicin with carboplatin are considered acceptable options.
  - Alternative schemes of paclitaxel and carboplatin administration, such as intraperitoneal administration or dense-dose regimens, have also been considered, however they are not supported as a standard of care due to the lack of confirmatory data.
- Targeted therapy: Bevacizumab (biologic, anti-VGEF-A antibody) as an add-on therapy to first-line chemotherapy is indicated for the front-line treatment of adult patients with advanced (International Federation of Gynaecology and Obstetrics [FIGO] stages III B, III C, and IV) epithelial ovarian, fallopian tube, or primary peritoneal cancer, followed by continued use of bevacizumab as a single agent until disease progression or for a maximum of 15 months or until unacceptable toxicity, whichever occurs earlier.

Surgery followed by first-line platinum-based chemotherapy is the standard treatment in most patients, improving their PFS and OS. Nevertheless, despite the initial response, approximately 70% of patients with advanced disease relapse and die within 5 years (Ledermann et al. 2013).

Example 3. Standard Therapy after First Recurrence of Platinum-Sensitive Ovarian Cancer The European Society of Medical Oncology (ESMO) established guidelines (Ledermann et al. 2013) of treatment options for therapy after first recurrence of platinum-sensitive ovarian cancer. It also includes recently authorized maintenance treatments.

- Second-line therapy: taxane in combination with a platinum compound (platinum doublet) is considered valuable, with other agent combinations tested in clinical trials, including trabectedin and pegylated liposomal doxorubicin. The choice should be based on the toxicity profile and convenience of administration.
- Targeted therapy: bevacizumab in combination with carboplatin and gemcitabine has been approved and is recommended in platinum-sensitive relapsed disease in patients not previously treated with bevacizumab.
- Maintenance treatments after second-line chemotherapy: olaparib, a PARP inhibitor, is indicated as monotherapy for the maintenance treatment of adult patients with platinum sensitive relapsed BRCA-mutated (germline and/or somatic) high-grade serous epithelial ovarian, fallopian tube, or primary peritoneal cancer who are in response (complete response or partial response) to platinum-based chemotherapy. Niraparib, another PARP inhibitor, is indicated for the maintenance treatment of adult patients with recurrent epithelial ovarian, fallopian tube, or primary peritoneal cancer who are in complete or partial response to platinum-based chemotherapy.

Despite great efforts to devise an optimal therapeutic approach to overcome the relapse following chemotherapy, only a limited number of treatment options remain available to patients with relapsed disease and the majority of such patients eventually die. Patients with disease recurrence are in high need of novel therapeutic options, such as a DC vaccine, which could improve their life expectancy and quality of life.

Example 4. Clinical Data in Newly Diagnosed Patients with Advanced Ovarian Cancer The study was conducted as an open label, multicenter, three-arm phase II clinical trial in women with newly diagnosed epithelial ovarian carcinoma, who have undergone debulking surgery. The aim of this study was to evaluate the efficacy and safety of the DC vaccine administered in parallel to chemotherapy as an add-on to standard of care chemotherapy with carboplatin and paclitaxel or sequentially after standard of care chemotherapy with carboplatin and paclitaxel compared to chemotherapy alone.

A total of 99 patients were centrally randomized in a ratio of 1:1:1 to treatment groups A (34 patients) to receive the DC vaccine in parallel with standard of care chemotherapy, B (34 patients) to receive the DC vaccine sequentially after standard of care chemotherapy, or C (31 patients) to receive standard of care chemotherapy alone.

Figure 1:
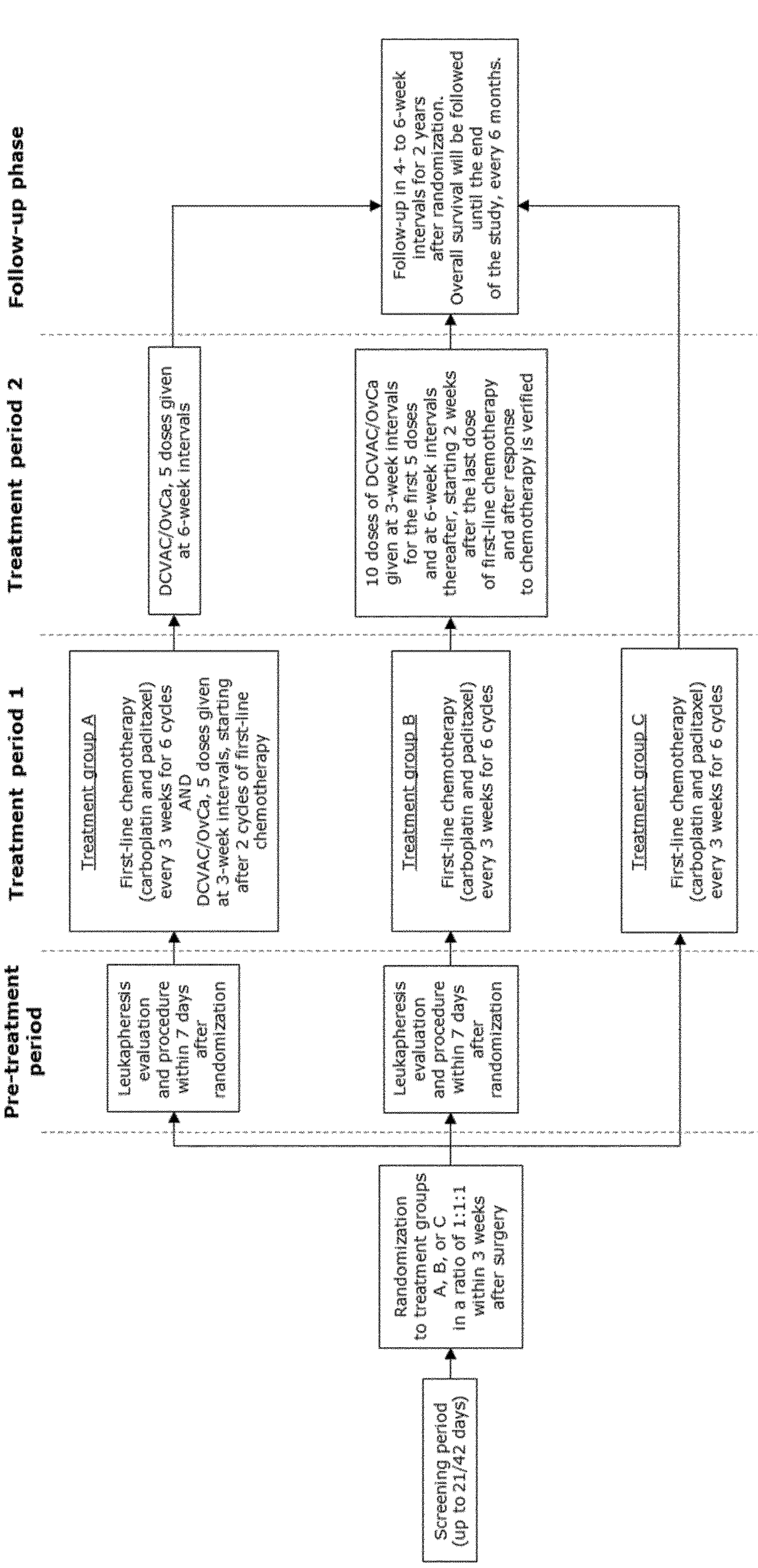
FIG. 1.

The DC vaccine was administered subcutaneously (SC) to patients in treatment groups A and B in up to 10 doses. The planned number of chemotherapy cycles was 6 in all treatment groups (FIG. 1).

The intent-to-treat (ITT) population included all randomized patients regardless of whether they received treatment or not; however, patients randomized to treatment groups A and B had to receive at least 1 dose of DC vaccine to be included in the ITT population (ITT: 31 patients in treatment group A [parallel DC vaccine], 30 patients in treatment group B [sequential DC vaccine], and 31 patients in treatment group C [standard of care]).

The per-protocol (PP) population included all randomized patients who received at least 3 cycles of standard of care chemotherapy and, for treatment groups A and B, at least 8 doses of DC vaccine, did not violate any inclusion criteria, and did not have any major protocol deviation (PP: 29 patients in treatment group A [parallel DC vaccine], 28 patients in treatment group B [sequential DC vaccine], and 30 patients in treatment group C [standard of care]).

The three treatment groups were balanced with regard to demographics and disease characteristics (Table 1). Exposure to chemotherapy and DC vaccine is summarized in Table 2.

TABLE 1

Baseline patient demographics and disease characteristics, ITT population

| | Treatment Group | | | |
|---|---|---|---|---|
| | A N = 31 | B N = 30 | C N = 31 | p-value |
| Age: mean ± SD, median (min-max) | 58.8 ± 12.1, 62 (24-73) | 55.6 ± 11.2, 56 (21-73) | 61.1 ±7.5, 62 (46-74) | 0.1266 |
| Race white: n (%) | 31 (100%) | 30 (100%) | 31 (100%) | 1.0000 |
| Type of epithelial cells | | | | |
| Endometrioid, n (%) | 2 (6.45%) | 6 (20.00%) | 1 (3.23%) | |
| Mucinous, n (%) | 0 (0.00%) | 0 (0.00%) | 0 (0.00%) | 0.0656 |
| Serous, n (%) | 29 (93.55%) | 24 (80.00%) | 30 (96.77%) | |
| Time since diagnosis*, days | | | | |
| Mean ± SD, median (min-max) | 26.4 ± 17.9, 21 (13-104) | 30.8 ± 18.1, 28 (8-94) | 25.2 ± 17.9, 21 (11-112) | 0.1574 |
| ECOG: mean ± SD, median (min-max) | 0.581 ± 0.720, 0 (0-2) | 0.600 ± 0.675, 0.5 (0-2) | 0.452 ± 0.675, 0 (0-2) | 0.5803 |

*to onset of 1st chemotherapy

Table 2: Treatment groups, ITT population

| | Treatment group | | |
|---|---|---|---|
| | A N = 31 | B N = 30 | C N = 31 |
| No. of 1st-line chemotherapy cycles: mean ± SD, median (min-max) | 5.90 ± 0.40, 6 (4-6) | 5.80 ± 0.76, 6 (3-6) | 5.68 ± 1.14, 6 (0-6) |
| No. of 1st-line chemotherapy non-responders: n (%) | 1 (3.23%) | 1 (3.33%) | 0 (0.00%) |
| No. of DC vaccine doses: mean ± SD, median (min-max) | 9.61 ± 1.43, 10 (3-10) | 9.47 ± 2.03, 10 (2-10) | Not applicable |
| No. of patients with DC vaccine continued beyond progression and administered together with 2nd-line chemotherapy: n (%) | 3 (9.68%) | 3 (10.00%) | Not applicable |
| Types of 2nd-line chemotherapy started | 1 patient: doxorubicin & | 1 patient: doxorubicin & | Not applicable |

-continued

Table 2: Treatment groups, ITT population

| | Treatment group | | |
|---|---|---|---|
| | A N = 31 | B N = 30 | C N = 31 |
| before completion of DC vaccine[a] | liposomal doxorubicin 1 patient: doxorubicin & gemcitabine 1 patient: topotecan | carboplatin 1 patient: cisplatin & doxorubicin & endoxan 1 patient: gemcitabine monotherapy | |

[a]The number provided to each second line therapy listed shows the number of patients with the particular treatment.

Results were calculated either by using as beginning of the trial period the time of first treatment or the time of randomization. Two pre-planned per protocol interim analyses of PFS and OS from the date of randomization were performed first at 6 months and second at 12 months after the last dose of standard of care chemotherapy of the last enrolled patient. Per protocol population excluded patients with DC vaccine production failure and protocol violations. The results from the two analyses were consistent. At the time of the second interim analysis, 40 progression events were reported (PFS data maturity 43.47%) and 14 patients died (OS data maturity 15.22%). The results from the second interim analysis are presented below. The median duration of patient follow-up at the time of the second interim analysis was 22.9 months (686 days) from the time of treatment and 22.8 months (694 days) from the time of randomization.

A log-rank test was used for comparing the PFS and OS distributions of the two treatment groups:

H01: PFS/OS group A=PFS/OS group C vs H11: PFS/OS group C≠PFS/OS group A,

H02: PFS/OS group B=PFS/OS group C vs H12: PFS/OS group C≠PFS/OS group B.

The hazard ratio (HR) was calculated using Cox proportional hazard regression. The estimate for the HR was based on fitting a proportional hazards regression model:

$$\lambda(t)=\lambda_0(t)*\exp(\beta z),$$

wherein $\lambda_0(t)$ is the baseline hazard function for group C, $\lambda(t)$ is the hazard function for group A/group B, z is a binary covariate (being 1 for group A/group B and 0 for group C), and $\exp(\beta)$ is the HR.

Efficacy in the ITT Population

The difference in OS between treatment group B (sequential DC vaccine) and C (standard of care) was statistically significant in favor of treatment group B (HR=0.13, p=0.0259 from the time of treatment, p=0.0.0251 from the time of randomization; Table 3, FIG. 2), meaning that the risk of death is reduced by 87%, compared to standard of care. Strikingly, in the sequential treatment group B, only one fatality was reported by the time of interim reporting, and this death even occurred during the chemotherapy phase of the trial, prior to any DCVAC treatment (see FIG. 2). Treatment groups A (parallel DC vaccine) and C (standard of care) were not statistically significantly different with regard to OS, with however a trend towards improved OS in treatment group A when compared to treatment group C (HR=0.64, p=0.4513 from the time of treatment, p=0.4460 from the time of randomization; Table 3, FIG. 2). Significance may not have been reached due to the relatively small size of the study. Clearly, fewer fatalities occurred in the parallel treatment group A than in the standard of care treatment group C (see FIG. 2).

Surprisingly, the data significantly show the superiority of the sequential administration of the DC vaccine after completion of first-line chemotherapy over standard chemotherapy alone as well as over DC vaccine administered in parallel with standard chemotherapy (see overall survival in FIG. 2). Treatment group B showed a significantly longer overall survival than treatment groups A and C. In particular group C showed the lowest OS after 3.5 years.

TABLE 3

Efficacy results from the second interim analysis in the study, ITT population

| | Treatment group B (sequential DC vaccine) over treatment group C (standard chemotherapy) | | | Treatment group A (parallel DC vaccine) over treatment group C (standard chemotherapy) | | |
|---|---|---|---|---|---|---|
| | HR | p-value | Benefit (assessed by medians in months) | HR | p-value | Benefit (assessed by medians in months) |
| OS | 0.13 | 0.0259 from time of treatment; 0.0251 from time of randomization | Medians not reached | 0.64 | 0.4513 fromtime of treatment; 0.4460 from time of randomization | Medians not reached |

Efficacy in the PP Population

The difference between treatment group B (sequential DC vaccine) and C (standard of care) was statistically significant in favor of treatment group B for OS (HR=0.00, p=0.0071 from the time of treatment, p=0.0068 from the time of randomization; Table 4, FIG. 3) meaning that after 3.5 years, no fatality occurred in the sequential treatment group B. Treatment groups A (parallel DC vaccine) and C (standard of care) were not statistically significantly different with regard to OS (HR=0.51, p=0.2777 from the time of treatment, p=0.2735 from the time of randomization; Table 4, FIG. 3), with however a trend towards improved OS in treatment group A when compared to treatment group C. Significance may not have been reached due to the relatively small size of the study. Clearly, fewer fatalities occurred in the parallel treatment group A than in the standard of care treatment group C (see FIG. 2).

Superiority of sequential administration of DC vaccine after completion of first-line chemotherapy over standard chemotherapy alone as well as over DC vaccine in parallel with standard chemotherapy shown above for the ITT population was therefore even more pronounced by the data for the PP population.

TABLE 4

| Second interim analysis, PP population | | | | | | |
|---|---|---|---|---|---|---|
| | Treatment group B (sequential DC vaccine) over treatment group C (standard of care) | | | Treatment group A (parallel DC vaccine) over treatment group C (standard of care) | | |
| | HR | p-value | Benefit (assessed by medians in months) | HR | p-value | Benefit (assessed by medians in months) |
| OS | 0.00 | 0.0071 from time of treatment; 0.0028 from time of randomization | Medians not reached | 0.51 | 0.2777 from time of treatment; 0.2735 from time of randomization | Medians not reached |

Overall, this clinical data surprisingly showed a significant and substantial overall survival benefit for patients randomized to the group receiving the DC vaccine sequentially after completion of first-line chemotherapy (group B), compared to standard of care (group C). Even more surprisingly, sequential administration of the DC vaccine (group B) was also significantly and substantially superior to DC vaccine administration in parallel with standard chemotherapy (group A).

It was also found that delivering multiple doses of the DC vaccine, preferentially at least 8 doses, to a patient was beneficiary to the patient. This can be inferred from the fact that the HR was lower in the PP population than in the ITT (the requirement for inclusion in the PP population was to receive at least 8 administrations of the DC vaccine and 3 cycles of standard of care chemotherapy).

Patient characteristics were balanced between treatment groups B (sequentially after completion of first-line chemotherapy) and C (only chemotherapy, no sequential treatment as a standard care) (see Table 1 and Table 2). Therefore, the observed significant efficacy advantage in treatment group B compared to treatment group C is not influenced by any demographic or standard chemotherapy response differences between these groups. The DC vaccine was administered to all patients in treatment group B who completed first-line chemotherapy.

The magnitude of the overall survival advantage when a DC vaccine is administered sequentially after first line chemotherapy underlines the potential of a DC vaccine to meet the unmet medical need for the sequential/maintenance treatment after first-line platinum-based chemotherapy, providing prolongation of time to disease progression and having a significant impact on the survival of patients with newly diagnosed advanced ovarian cancer. The impact of such a DC vaccine on treatment of ovarian cancer is further highlighted by the fact that until now no therapy has been approved to be started after completion of first-line therapy for advanced ovarian cancer (maintenance or sequential treatment).

Safety Data on the DC Vaccine

In treatment group A, 14 SAEs were reported in 8 patients before the start of DC vaccine trial treatment and 14 SAEs were reported in 9 patients after the start of DC vaccine trial treatment. In treatment group B, 20 SAEs were reported in 7 patients before the start of DC vaccine trial treatment and 9 SAEs were reported in 5 patients after the start of DC vaccine trial treatment. In treatment group C, 14 SAEs were reported in 9 patients, although on a shorter reporting time period.

The most frequently reported SAEs were the following:

Neutropenia: 8 SAEs in 7 patients

Anemia: 7 SAEs in 6 patients

Thrombocytopenia: 4 SAEs in 2 patients

Ascites: 5 SAEs in 2 patients

Infected lymphocele: 5 SAEs in 5 patients

The safety data above indicated that the DC vaccine (including leukapheresis) was well tolerated and that there were no safety-related issues associated with the DC vaccine administration, regardless of whether the DC vaccine was administered together with chemotherapy or sequentially after chemotherapy. No potential risks have been detected or confirmed in the clinical trials.

Example 5. Advantage of a DC Vaccine Over Existing Maintenance Therapy

Presently, a certain number of ovarian cancer patients undergoing first-line chemotherapy with carboplatin and paclitaxel are treated with bevacizumab as an add-on in combination with carboplatin and paclitaxel followed by bevacizumab as monotherapy as maintenance therapy until disease progression or for a maximum of 15 months or until unacceptable toxicity, whichever occurs earlier.

Based on the clinical study described above, it was calculated how the DC vaccine administration compares the effect of bevacizumab maintenance therapy in first-line patients of ovarian carcinoma as reported (Bevacizumab SmPC, 'Avastin Summary of Product Characteristics').

Significant Prolongation of Patient Survival

The survival benefit for patients receiving the DC vaccine after first-line chemotherapy as compared to patients not treated with the DC vaccine (PP: HR=0.00, p=0.0071 from the time of treatment, p=0.0068 from the time of randomization; ITT: HR=0.13, p=0.0259 from the time of treatment, p=0.0251 from the time of randomization) is higher than that of continuous bevacizumab administration compared to patients not treated with bevacizumab (bevacizumab 15 mg/kg: HR=0.88, p=0.0641; bevacizumab 7.5 mg/kg: HR=0.99, p=0.8910; Table 6). Most notably, the difference in OS and PFS between DC vaccine-treated patients and patients not receiving the DC vaccine was statistically significant (ITT: p=0.02519 from the time of treatment, p=0.0251 from the time of randomization; Table 6).

TABLE 6

Commented overview of the DC vaccine administered sequentially after first-line carboplatin and paclitaxel and authorised bevacizumab administered after first-line carboplatin and paclitaxel

| | Administration | | Efficacy | | |
|---|---|---|---|---|---|
| Regimen | Dose and schedule | Duration of treatment | PFS (HR, p) | OS (HR, p) | Safety |
| DC vaccine sequentially after 1st-line chemotherapy | ca 1 × $10^7$ DCs as two 2.5 mL injections SC q3w + q6w | up to approximately 10 months | 0.43 0.0510[a] 0.0516[b] | 0.13 0.0259[a] 0.0251[b] | No potential risks have been detected or confirmed in clinical trials with DC vaccine |
| Bevacizumab continuous after bevacizumab combination with carboplatin/ paclitaxel | 15 mg/kg IV q3w | 15 months | 0.7[c] <0.0001 | 0.88[c] 0.0641 | Patients treated with bevacizumab may be at an increased risk for the development of various side effects, e.g.[c]: gastrointestinal perforation and fistulae, wound healing complications, hyper-tension, posterior reversible encephalopathy syndrome, thrombo-embolism or haemorrhage, congestive heart failure, neutropenia and infections, hypersensitivity reactions/infusion reactions, osteonecrosis of the jaw |
| Bevacizumab continuous after bevacizumab combination with carboplatin/ paclitaxel | 7.5 mg/kg IV q3w | 12 months | 0.86[c] 0.0185 | 0.99[c] 0.8910 | |

[a]Measured from the time of treatment
[b]Measured from the time of randomization
[c]Bevacizumab SmPC ('Avastin Summary of Product Characteristics')
IV, intravenous;
q3w, every 3 weeks;
q6w, every 6 weeks;
p, p-value Therefore, the DC vaccine administered after first-line therapy with carboplatin and paclitaxel appears to be superior to bevacizumab maintenance therapy and shows the potential to fulfil the unmet medical need of patients with newly diagnosed ovarian cancer for a treatment which would prolong survival without adding further toxicity to existing treatments.

Easy DC Vaccine Administration and High Patient Compliance with DC Vaccine Treatment The DC vaccine was administered to the patients subcutaneously; one dose was divided into two 2.5 mL injections (Table 6). Neither the administration volume nor the route resulted in significant discomfort to the patient. This administration did not require hospital stay and extensive patient monitoring and was well tolerated by patients, which facilitated patient compliance with the treatment.

The patients' perception of being treated with an autologous product was very positive, adding no further discomfort to the standard chemotherapy regimen. In addition, the same dose of DC vaccine, i.e. approximately $1\times10^7$ DCs, was administered to all patients, so the risk of dosage errors was minimal.

The fact that there was neither an apparent need for regular patient visits to the hospital and scheduled examinations for the monitoring of potential treatment-emergent side effects, nor a need for the prescription of co-medication for potential side effects may bring major advantage for the overall patient management.

Because of the benign safety profile of the DC vaccine, no special precautions were needed in case the patient needed other treatments, and no considerations were needed for any dose adjustments of the patient's concomitant medications for concurrent underlying conditions, which is beneficial for the patient's daily routine and reduction of the number of hospital visits and check-ups.

Leukapheresis, a procedure to collect PBMCs for DC vaccine manufacturing, can be considered an intervention and a potential source of discomfort for the patient. Nevertheless, the procedure is well tolerated by patients and did not raise any concerns or represent a limiting factor for the treatment.

REFERENCES

'American Cancer Society—How Chemotherapy Drugs Work'. 2016. American Cancer Society, Accessed 2018 Jan. 5. www.cancer.org/treatment/treatments-and-side-effects/treatment-types/chemotherapy/how-chemo-therapy-drugs-work.html.

'Avastin Summary of Product Characteristics'. Accessed Oct. 9, 2017. www.ema.europa.eu/docs/en GB/document library/EPAR—Product Information/human/000582/WC500029271.pdf.

Banchereau, J., and R. M. Steinman. 1998. 'Dendritic cells and the control of immunity', *Nature,* 392: 245-52.

Berd, D., and M. J. Mastrangelo. 1987. 'Effect of low dose cyclophosphamide on the immune system of cancer patients: reduction of T-suppressor function without depletion of the CD8+ subset', *Cancer Res,* 47: 3317-21.

Bloy, N., J. Pol, F. Aranda, A. Eggermont, I. Cremer, W. H. Fridman, J. Fucikova, J. Galon, E. Tartour, R. Spisek, M. V. Dhodapkar, L. Zitvogel, G. Kroemer, and L. Galluzzi. 2014. 'Trial watch: Dendritic cell-based anticancer therapy', *Oncoimmunology,* 3: e963424.

CancerTherapyAdvisor. 2017a. 'NON-SMALL CELL LUNG CANCER TREATMENT REGIMENS', Accessed 2017 Nov. 24. www.cancertherapyadvisor.com/lung-cancerlung-cancer-nsclc-treatment-regimens/article/527545/.

2017b. 'OVARIAN CANCER TREATMENT REGIMENS', Accessed 2017 Nov. 24. www.cancertherapyadvisor.com/gynecologic-cancer/ovarian-cancer-treatment-regimens/article/218127/.

2017c. 'PROSTATE CANCER TREATMENT REGIMENS', Accessed 2017 Nov. 24. www.cancertherapyadvisor.com/prostate-cancer/prostate-cancer-treatment-regimens/article/218186/?DCMP=OTC-cta_regasset.

Dong, W., R. Wei, H. Shen, Y. Ni, L. Meng, and J. Du. 2016. 'Combination of DC Vaccine and Conventional Chemotherapeutics', *Anticancer Agents Med Chem,* 16: 558-67.

Ellis, P. M. 2016. 'Anti-angiogenesis in Personalized Therapy of Lung Cancer', *Adv Exp Med Biol,* 893: 91-126.

Elster, J. D., D. K. Krishnadas, and K. G. Lucas. 2016. 'Dendritic cell vaccines: A review of recent developments and their potential pediatric application', *Hum Vaccin Immunother,* 12: 2232-9.

'FIGO ovarian cancer staging'. 2014. Accessed Sep. 14, 2017. https://www.sgo.org/wp-content/uploads/2012/09/FIGO-Ovarian-Cancer-Staging 1.10.14.pdf.

Fucikova, J., I. Moserova, I. Truxova, I. Hermanova, I. Vancurova, S. Partlova, A. Fialova, L. Sojka, P. F. Cartron, M. Houska, L. Rob, J. Bartunkova, and R. Spisek. 2014. 'High hydrostatic pressure induces immunogenic cell death in human tumor cells', *Int J Cancer,* 135: 1165-77.

Fucikova, J., M. Podrazil, L. Jarolim, P. Bilkova, M. Hensler, E. Becht, Z. Gasova, J. Klouckova, J. Kayserova, R. Horvath, A. Fialova, K. Vavrova, K. Sochorova, D. Rozkova, R. Spisek, and J. Bartunkova. 2017. 'Phase I/II trial of dendritic cell-based active cellular immunotherapy with DCVAC/PCa in patients with rising PSA after primary prostatectomy or salvage radiotherapy for the treatment of prostate cancer', *Cancer Immunol Immunother.*

Galluzzi, L., L. Senovilla, E. Vacchelli, A. Eggermont, W. H. Fridman, J. Galon, C. Sautes-Fridman, E. Tartour, L. Zitvogel, and G. Kroemer. 2012. 'Trial watch: Dendritic cell-based interventions for cancer therapy', *Oncoimmunology,* 1: 1111-34.

Garg, A. D., M. Vara Perez, M. Schaaf, P. Agostinis, L. Zitvogel, G. Kroemer, and L. Galluzzi. 2017. 'Trial watch: Dendritic cell-based anticancer immunotherapy', *Oncoimmunology,* 6: e1328341.

Ledermann, J. A., F. A. Raja, C. Fotopoulou, A. Gonzalez-Martin, N. Colombo, C. Sessa, and Esmo Guidelines Working Group. 2013. 'Newly diagnosed and relapsed epithelial ovarian carcinoma: ESMO Clinical Practice Guidelines for diagnosis, treatment and follow-up', *Ann Oncol,* 24 Suppl 6: vi24-32.

'National Cancer Institute—Diagnosis and Staging'. 2015. National Cancer Institute, Accessed 2017 Dec. 8. www.cancer.gov/about-cancer/diagnosis-staging/staging.

Palucka, K., and J. Banchereau. 2013. 'Dendritic-cell-based therapeutic cancer vaccines', *Immunity,* 39: 38-48.

Sakarya, D. K.; Yetimalar, M. H. 2016. 'Is there a current change of maintenance treatment in ovarian cancer? An updated review of the literature', *JBUON,* 21: 290-300.

Turnis, M. E., and C. M. Rooney. 2010 'Enhancement of dendritic cells as vaccines for cancer', *Immunotherapy,* 2: 847-62.

Vacchelli, E., I. Vitale, A. Eggermont, W. H. Fridman, J. Fucikova, I. Cremer, J. Galon, E. Tartour, L. Zitvogel, G. Kroemer, and L. Galluzzi. 2013. 'Trial watch: Dendritic cell-based interventions for cancer therapy', *Oncoimmunology,* 2: e25771.

Verma, R., R. E. Foster, K. Horgan, K. Mounsey, H. Nixon, N. Smalle, T. A. Hughes, and C. R. Carter. 2016. 'Lymphocyte depletion and repopulation after chemotherapy for primary breast cancer', *Breast Cancer Res,* 18: 10.

WO 2013/004708

WO 2015/097037

What is claimed:

1. A method of treatment of ovarian cancer in a patient comprising administering to the patient a chemotherapy and a dendritic cell vaccine, wherein the chemotherapy consists of a combination treatment of paclitaxel and carboplatin and wherein the dendritic cell vaccine is administered to the patient after completion of the chemotherapy, Wherein:

the dendritic cells are loaded ex vivo with whole ovarian tumor cells killed by high hydrostatic pressure, from 5 to 30 doses of dendritic cell vaccines are administered, and the cancer is Stage II-IV newly diagnosed ovarian cancer prior to the administration of first dose of the chemotherapy, wherein the first dose of the dendritic cell vaccine is administered within two months after administration of last dose of the chemotherapy.

2. The method of claim 1, wherein the first dose of the dendritic cell vaccine is administered within one month after administration of the last dose of the chemotherapy.

3. The method of claim 1, wherein the dendritic cell vaccine is administered in combination with a maintenance therapy.

4. The method of claim 1, wherein the whole ovarian tumor cells are allogeneic to the patient or originate from one or multiple ovarian tumor cell lines.

5. The method of claim 1, wherein the dendritic cells are obtained from monocytes cultivated in the presence of cytokines, wherein the monocytes are obtained by leukapheresis prior to the chemotherapy.

6. The method of claim 1, wherein i) the dendritic cell vaccine doses are administered at 1-week intervals, at 2-week intervals, at 3-week intervals, at 5-week intervals or at 6-week intervals; and/or ii) the dosing schedule of the dendritic cell vaccine comprises 5 initial doses administered at 3-week intervals followed by 5 doses at 3-week intervals or 6-week intervals.

7. The method of claim 6, wherein 8 to 15 doses of dendritic cell vaccines are administered.

8. The method of claim 1, wherein the first dose of the dendritic cell vaccine is administered within two weeks after administration of the last dose of the chemotherapy.

* * * * *